United States Patent

Kulagowski et al.

[11] Patent Number: 5,814,644
[45] Date of Patent: Sep. 29, 1998

[54] INDOLE DERIVATIVES AS DOPAMINE D4 ANTAGONISTS

[75] Inventors: Janusz Jozef Kulagowski, Bishops Stortford, United Kingdom; Paul David Leeson, Monmouth Junction, N.J.; Mark Peter Ridgill, Watton-At-Stone, United Kingdom

[73] Assignee: Merck Sharp & Dohme, Ltd., Hoddesdon, England

[21] Appl. No.: 532,780

[22] PCT Filed: Apr. 8, 1994

[86] PCT No.: PCT/GB94/00760

§ 371 Date: Apr. 8, 1996

§ 102(e) Date: Apr. 8, 1996

[87] PCT Pub. No.: WO94/24105

PCT Pub. Date: Oct. 27, 1994

[30] Foreign Application Priority Data

Apr. 15, 1993 [GB] United Kingdom ............ 9307831
Aug. 5, 1993 [GB] United Kingdom ............ 9316274

[51] Int. Cl.⁶ .................. A61K 31/44; A61K 31/445; C07D 401/06; C07D 403/06
[52] U.S. Cl. ................ 514/323; 514/339; 546/201; 546/277.4
[58] Field of Search .................. 514/323, 339; 546/201, 277.4

[56] References Cited

U.S. PATENT DOCUMENTS

| | | | |
|---|---|---|---|
| 3,188,313 | 6/1965 | Archer | 544/364 |
| 3,412,097 | 11/1968 | Corts et al. | 546/197 |
| 5,256,673 | 10/1993 | Bottcher et al. | 514/338 |
| 5,432,177 | 7/1995 | Baker et al. | 514/253 |

FOREIGN PATENT DOCUMENTS 0 411 631 A1  2/1991  WIPO.

OTHER PUBLICATIONS

Chemical Abstracts, 1967 vol. 66 p. 2728, Abs. No. 28694r, Potts et al "Synthetic Experiments Relating to Indole Alkaloids . . .".

Primary Examiner—Alan L. Rotman
Attorney, Agent, or Firm—Philippe L. Durette; Melvin Winokur

[57] ABSTRACT

Compound of formula (I), or a pharmaceutically acceptable salt thereof or a prodrug thereof wherein E represents $-CH_2-$ or $-CH_2CH_2-$; R represents hydrogen or $C_{1-6}$ alkyl; Q represents a moiety of formula Qa, Qb, Qc or Qd which are antagonists of dopamine receptor subtypes within the brain, having a selective affinity for the dopamine $D_4$ receptor subtype over other dopamine receptor subtypes, and are accordingly of benefit in the treatment and/or prevention of psychotic disorders such as schizophrenia whilst manifesting fewer side-effects than those associated with classical neuroleptic drugs.

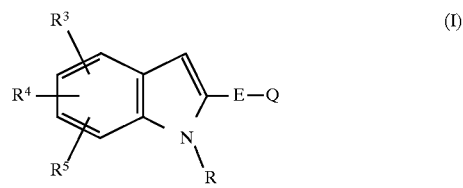

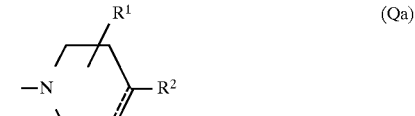

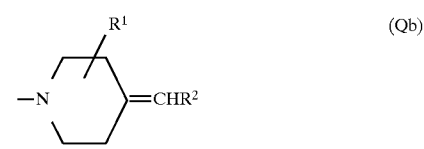

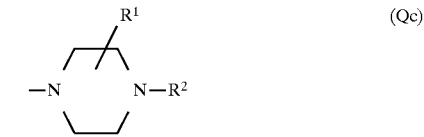

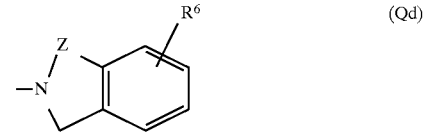

13 Claims, No Drawings

INDOLE DERIVATIVES AS DOPAMINE D4 ANTAGONISTS

This invention relates to the use of a particular class of heteroaromatic compounds. More particularly, the invention is concerned with the use of substituted indole derivatives which are antagonists of dopamine receptor subtypes within the brain and are therefore of benefit in the treatment and/or prevention of psychotic disorders such as schizophrenia.

The "dopamine hypothesis" of schizophrenia predicts an increased activity of dopamine neurotransmission in the disease. The hypothesis is supported by early observations that drugs, such as amphetamine, with dopamine agonist or dopamine-releasing properties are capable of eliciting a psychosis indistinguishable from acute paranoid schizophrenia.

Schizophrenia is a disorder which is conventionally treated with drugs known as neuroleptics. In the majority of cases, the symptoms of schizophrenia can be treated successfully with so-called "classical" neuroleptic agents such as haloperidol. Classical neuroleptics generally are antagonists at dopamine $D_2$ receptors. The fact that classical neuroleptic drugs have an action on dopamine receptors in the brain thus lends credence to the "dopamine hypothesis" of schizophrenia.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London), 1991, 350, 610) and $D_5$ (Sunahara et al., Nature (London), 1991, 350, 614) receptor subtypes have been described.

Notwithstanding their beneficial antipsychotic effects, classical neuroleptic agents such as haloperidol are frequently responsible for eliciting acute extrapyramidal symptoms and neuroendocrine disturbances. These side-effects, which clearly detract from the clinical desirability of classical neuroleptics, are believed to be attributable to $D_2$ receptor blockade in the striatal region of the brain. It is considered (Van Tol et al., supra) that compounds which can interact selectively with the dopamine $D_4$ receptor subtype, whilst having a less-pronounced action at the $D_2$ subtype, might be free from, or at any rate less prone to, the side-effects associated with classical neuroleptics, whilst at the same time maintaining a beneficial level of antipsychotic activity.

The compounds of use in the present invention, being antagonists of dopamine receptor subtypes within the brain, are accordingly of benefit in the treatment and/or prevention of psychotic disorders such as schizophrenia. Moreover, the compounds of use in the invention have a selective affinity for the dopamine $D_4$ receptor subtype over other dopamine receptor subtypes, in particular the $D_2$ subtype, and can therefore be expected to manifest fewer side-effects than those associated with classical neuroleptic drugs.

U.S. Pat. No. 3,188,313 describes inter alia certain 1-[(2-indolyl)-lower-alkyl]-4-substituted-piperazines, which are alleged therein to possess a panoply of depressant actions on the central and autonomic nervous system, the cardiovascular system and the skeletal-muscular system, including blood pressure lowering, vomiting incidence decreasing, sleeping time potentiating, tranquilizing and skeletal muscle relaxing activities. They are consequently alleged to be useful as hypotensive agents, antinauseants, antipyretics, sedatives, tranquilizers and skeletal muscle relaxants.

In addition, NL-A-6511642 describes a family of 2-[piperidinoalkyl]-1H-indole derivatives, which are stated therein to have analgesic and muscle relaxant activity.

There is, however, no suggestion in U.S. Pat. No. 3,188,313 or NL-A-6511642 that the compounds described therein would be of any benefit in the treatment and/or prevention of psychotic disorders such as schizophrenia, still less that in doing so they might be expected to manifest fewer side-effects than those exhibited by classical neuroleptic agents.

The present invention accordingly provides the use of a compound of formula I, or a pharmaceutically acceptable salt thereof or a prodrug thereof:

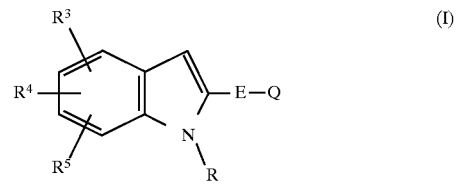
(I)

wherein
E represents —CH$_2$— or —CH$_2$CH$_2$—;
R represents hydrogen or C$_{1-6}$ alkyl;
Q represents a moiety of formula Qa, Qb, Qc or Qd:

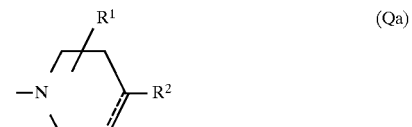
(Qa)

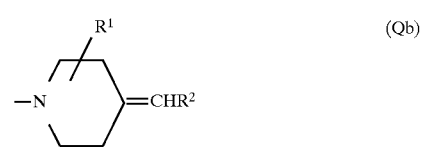
(Qb)

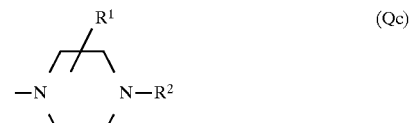
(Qc)

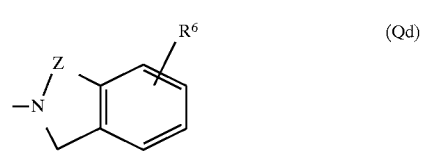
(Qd)

in which the broken line represents an optional chemical bond;

R$^1$ represents hydrogen, or an optionally substituted C$_{1-6}$ alkyl, C$_{1-6}$ alkoxy, C$_{2-6}$ alkenyl, C$_{2-6}$ alkynyl, aryl, aryl(C$_{1-6}$)alkyl, aryl(C$_{1-6}$)alkoxy, aryl(C$_{2-6}$) alkenyl, aryl(C$_{2-6}$)alkynyl, C$_{3-7}$ heterocycloalkyl (C$_{1-6}$) alkyl, heteroaryl, heteroaryl(C$_{1-6}$)alkyl, heteroaryl(C$_{2-6}$)alkenyl or heteroaryl(C$_{2-6}$)alkynyl group;

R$^2$ represents an optionally substituted C$_{1-6}$ alkyl, C$_{1-6}$ alkoxy, C$_{2-6}$ alkenyl, C$_{2-6}$ alkynyl, aryl, aryl(C$_{1-6}$) alkyl, aryl(C$_{1-6}$)alkoxy, aryl(C$_{2-6}$)alkenyl, aryl(C$_{2-6}$) alkynyl, C$_{3-7}$ heterocycloalkyl(C$_{1-6}$)alkyl, heteroaryl, heteroaryl(C$_{1-6}$)alkyl, heteroaryl(C$_{2-6}$) alkenyl or heteroaryl(C$_{2-6}$)alkynyl group;

R$^3$, R$^4$ and R$^5$ independently represent hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$;

Z represents —CH$_2$— or —CH$_2$CH$_2$—;

R$^6$ represents hydrogen, C$_{1-6}$ alkyl, C$_{1-6}$ alkoxy, aryl, aryl(C$_{1-6}$)alkyl or halogen; and R$^a$ and R$^b$ independently represent hydrogen, hydrocarbon or a heterocyclic group; for the manufacture of a medicament for the treatment and/or prevention of psychotic disorders such as schizophrenia.

For use in medicine, the salts of the compounds of formula I will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of use in the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, aryl, aryl(C$_{1-6}$)alkyl, aryl(C$_{2-6}$)alkenyl and aryl(C$_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl, heteroaryl(C$_{1-6}$)alkyl, heteroaryl(C$_{2-6}$)alkenyl and heteroaryl(C$_{2-6}$)alkynyl groups.

Suitable alkyl groups within the scope of the term "hydrocarbon" and within the definition of the substituents R, R$^1$, R$^2$ and R$^6$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups within the scope of the term "hydrocarbon" and within the definition of the substituents R$^1$ and R$^2$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents R$^1$ and R$^2$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents R$^1$, R$^2$ and R$^6$ include phenyl and naphthyl.

Particular aryl(C$_{1-6}$)alkyl groups within the scope of the term "hydrocarbon" and within the definition of the substituents R$^1$, R$^2$ and R$^6$ include benzyl, naphthylmethyl, phenethyl and phenylpropyl.

Suitable heterocycloalkyl groups include azetidinyl, pyrrolidyl, piperidyl, piperazinyl, morpholinyl and tetrahydrofuryl groups.

A particular C$_{3-7}$ heterocycloalkyl(C$_{1-6}$)alkyl group within the scope of the expression "a heterocyclic group" and within the definition of the substituents R$^1$ and R$^2$ is tetrahydrofurylethyl.

Suitable heteroaryl groups within the scope of the expression "a heterocyclic group" and within the definition of the substituents R$^1$ and R$^2$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl(C$_{1-6}$)alkyl groups within the scope of the expression "a heterocyclic group" and within the definition of the substituents R$^1$ and R$^2$ include thienylmethyl, pyridylmethyl, pyrimidinylmethyl and pyrazinylmethyl.

The hydrocarbon and heterocyclic groups, as well as the substituents R$^1$ and R$^2$, may in turn be optionally substituted by one or more groups selected from C$_{1-6}$ alkyl, adamantyl, phenyl, aryl(C$_{1-6}$)alkyl, halogen, C$_{1-6}$ haloalkyl, C$_{1-6}$ aminoalkyl, trifluoromethyl, hydroxy, C$_{1-6}$ alkoxy, aryloxy, keto, C$_{1-3}$ alkylenedioxy, nitro, cyano, carboxy, C$_{2-6}$ alkoxycarbonyl, C$_{2-6}$ alkoxycarbonyl(C$_{1-6}$)alkyl, C$_{2-6}$ alkylcarbonyloxy, arylcarbonyloxy, C$_{2-6}$ alkylcarbonyl, arylcarbonyl, C$_{1-6}$ alkylthio, C$_{1-6}$ alkylsulphinyl, C$_{1-6}$ alkylsulphonyl, arylsulphonyl, trifluoromethanesulphonyloxy, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —PO(OR$^v$)(OR$^w$), —CONR$^v$R$^w$, —SO$_2$NR$^v$R$^w$ and —CH$_2$SO$_2$NR$^v$R$^w$, in which R$^v$ and R$^w$ independently represent hydrogen, C$_{1-6}$ alkyl, aryl or aryl(C$_{1-6}$)alkyl.

The term "halogen" as used herein includes fluorine, chlorine, bromine and iodine, especially chlorine.

The present invention includes within its scope the use of prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds of use in the invention have at least one asymmetric centre, they may accordingly exist as enantiomers. Where the compounds of use in the invention possess two or more asymmetric centres, they may additionally exist as diastereoisomers. It is to be understood that the use of all such isomers and mixtures thereof is encompassed within the scope of the present invention.

Suitably, the substituent R represents hydrogen or methyl, especially hydrogen.

Suitably, the substituent R$^1$ represents hydrogen.

Suitable values for the substituent R$^2$ include C$_{1-6}$ alkyl, phenyl, halophenyl, C$_{1-6}$ alkylphenyl, C$_{1-6}$ alkoxyphenyl, nitrophenyl, benzyl, halobenzyl, phenethyl, phenylpropyl and benzyloxy. Particular values of R$^2$ include methyl, ethyl, n-propyl, isopropyl, phenyl, chlorophenyl, ethylphenyl, methoxyphenyl, nitrophenyl, benzyl, chlorobenzyl, phenethyl, phenylpropyl and benzyloxy.

Suitable values for the substituents R$^3$, R$^4$ and R$^5$ include hydrogen, halogen, cyano, nitro, trifluoromethyl, amino, C$_{1-6}$ alkylamino, di(C$_{1-6}$)alkylamino, C$_{1-6}$ alkyl, C$_{1-6}$ alkoxy, aryl(C$_{1-6}$)alkoxy and C$_{2-6}$ alkylcarbonyl. Particular values include hydrogen, fluoro, chloro, methyl, methoxy and benzyloxy.

Particular values of $R^6$ include hydrogen, phenyl, chloro and bromo.

A particular sub-class of compounds of use in the invention is represented by the compounds of formula IIA, and pharmaceutically acceptable salts thereof and prodrugs thereof:

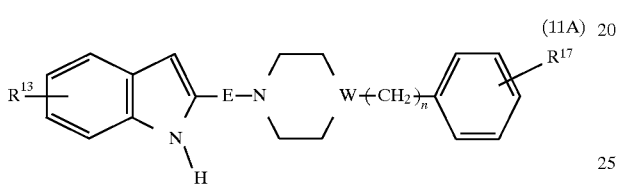
(11A)

wherein

E is as defined with reference to formula I above;

n is zero, 1, 2 or 3;

W is CH or nitrogen; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

Particular values of $R^{13}$ include hydrogen, fluoro, chloro, methyl, ethyl, methoxy and benzyloxy.

Particular values of $R^{17}$ include hydrogen, chloro, methoxy and nitro.

Another sub-class of compounds of use in the invention is represented by the compounds of formula IIB, and pharmaceutically acceptable salts thereof and prodrugs thereof:

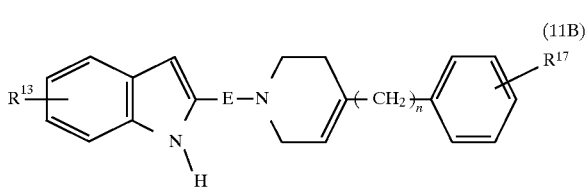
(11B)

wherein

E is as defined with reference to formula I above; and n, $R^{13}$ and $R^{17}$ are as defined with reference to formula IIA above.

A further sub-class of compounds of use in the invention is represented by the compounds of formula IIC, and pharmaceutically acceptable salts thereof and prodrugs thereof:

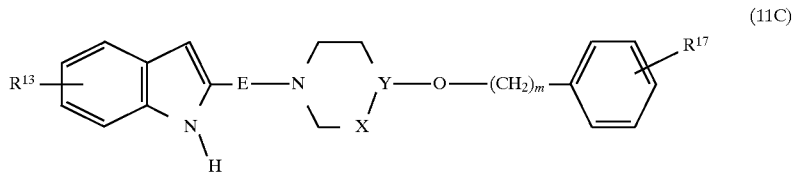
(11C)

wherein m is 1, 2 or 3;

—X—Y— represents —CH$_2$CH— or —CH=C—;

E is as defined with reference to formula I above; and $R^{13}$ and $R^{17}$ are as defined with reference to formula IIA above.

A still further sub-class of compounds of use in the invention is represented by the compounds of formula IID, and pharmaceutically acceptable salts thereof and prodrugs thereof:

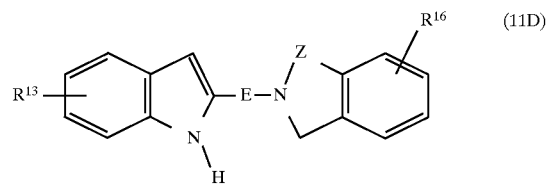
(11D)

wherein

E is as defined with reference to formula I above;

Z represents —CH$_2$— or —CH$_2$CH$_2$—;

$R^{13}$ is as defined with reference to formula IIA above; and $R^{16}$ represents hydrogen, $C_{1-6}$ alkyl, $C_{1-6}$ alkoxy, aryl, aryl($C_{1-6}$)alkyl or halogen.

Particular values of $R^{16}$ include hydrogen, phenyl, chloro and bromo, especially hydrogen.

A yet further sub-class of compounds of use in the invention is represented by the compounds of formula IIE, and pharmaceutically acceptable salts thereof and prodrugs thereof:

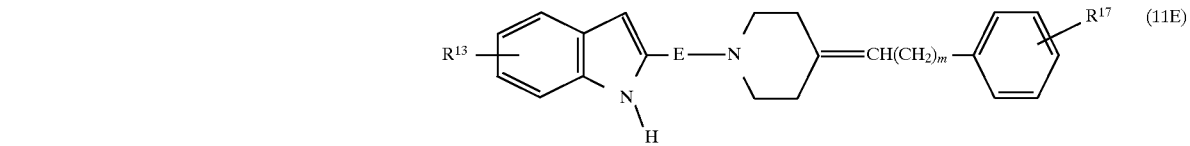
(11E)

wherein

E is as defined with reference to formula I above;

$R^{13}$ and $R^{17}$ are as defined with reference to formula IIA above; and m is 1, 2 or 3.

Specific compounds of use in the present invention include:

2-(4-phenylpiperazin-1-ylmethyl)-1H-indole;

2-[4-(4-chlorophenyl)piperazin-1-ylmethyl]-1H-indole;

and pharmaceutically acceptable salts thereof and prodrugs thereof.

Certain compounds falling within the definition of formula I above are novel. Particular sub-classes of novel compounds in accordance with the present invention comprise the compounds of formulae IIB, IIC, IID and IIE as defined above, and salts and prodrugs thereof. The invention further provides a novel compound selected from the following:

2-(4-benzylpiperazin-1-ylmethyl)-1H-indole;
2-[2-(4-benzylpiperazin-1-yl)ethyl]-1H-indole;
2-[4-(4-methoxyphenyl)piperazin-1-ylmethyl]-1H-indole;
2-(4-phenyl-1,2,3,6-tetrahydropyrid-1-ylmethyl)-1H-indole;
2-[4-(2-phenylethyl)piperidin-1-ylmethyl]-1H-indole;
2-(4-benzyloxypiperidin-1-ylmethyl)-1H-indole;
2-[4-(2-phenylethyl)-1,2,3,6-tetrahydropyrid-1-ylmethyl]-1H-indole;
2-[4-(3-phenylpropyl)-1,2,3,6-tetrahydropyrid-1-ylmethyl]-1H-indole;
2-[4-(3-phenylpropylidene)piperidin-1-ylmethyl]-1H-indole;
2-(1,2,3,4-tetrahydroisoquinolin-2-ylmethyl)-1H-indole;
2-(1,2-dihydroisoindol-2-ylmethyl)-1H-indole;
and salts and prodrugs thereof.

The invention also provides pharmaceutical compositions comprising one or more of the novel compounds according to the invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I above, including the novel compounds according to the present invention, may be prepared by a process which comprises reacting a compound of formula III with a compound of formula IV:

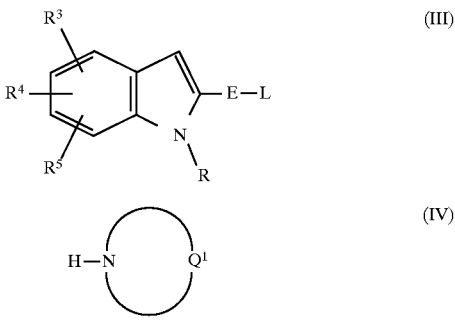

wherein E, R, $R^3$, $R^4$ and $R^5$ are as defined above, $Q^1$ represents the residue of a moiety of formula Qa to Qd as defined above, and L represents a suitable leaving group.

The leaving group L is suitably a halogen atom, e.g. chlorine or bromine.

The reaction is conveniently carried out by stirring the reactants under basic conditions in a suitable solvent, for example potassium carbonate in N,N-dimethylformamide, or triethylamine in tetrahydrofuran or acetonitrile.

In an alternative procedure, the compounds of formula I above, including the novel compounds according to the present invention, may be prepared by a process which comprises reducing a compound of formula V:

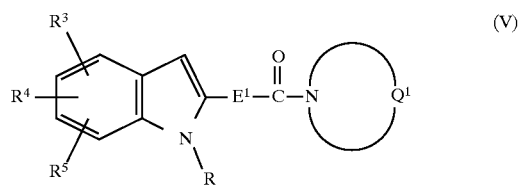

wherein $Q^1$, R, $R^3$, $R^4$ and $R^5$ are as defined above; and $E^1$ represents a bond or a methylene group.

The reaction is conveniently carried out by treating the compound V with a reducing agent such as lithium aluminium hydride in an appropriate solvent, e.g. tetrahydrofuran.

The intermediates of formula V above may suitably be prepared by reacting a compound of formula IV as defined above with a compound of formula VI:

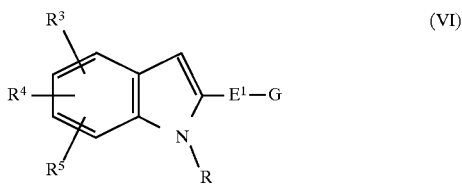

wherein R, $R^3$, $R^4$, $R^5$ and $E^1$ are as defined above; and G represents a reactive carboxylate moiety.

Suitable values for the reactive carboxylate moiety G include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula VI above wherein G is an acid chloride moiety may be prepared by treating the corresponding carboxylic acid derivative with thionyl chloride in toluene. Similarly, the intermediates of formula VI wherein G is an acylimidazole moiety may be prepared by treating the corresponding carboxylic acid derivative with 1,1'-carbonyldiimidazole. Alternatively, the reactive carboxylate moiety G may be obtained by treating the corresponding compound wherein G is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula IV.

In a further procedure, the compounds of formula I above, including the novel compounds according to the invention, may be prepared by a process which comprises the ring closure of a compound of formula VII:

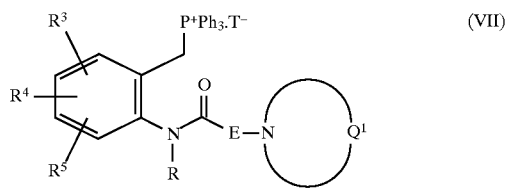

wherein R, $R^3$, $R^4$, $R^5$, E and $Q^1$ are as defined above; and $T^-$ represents a suitable counterion, e.g. a halide ion such as bromide.

The ring closure reaction is conveniently carried out under conditions analogous to those described in *Chem. Ber.*, 1986, 119, 2069–2074. This requires the presence of a strong base, typically potassium t-butoxide; and the reaction is suitably effected in an inert organic solvent at an elevated temperature, for example toluene at reflux.

The intermediates of formula VII above may suitably be prepared by reacting a compound of formula IV as defined above with a compound of formula VIII:

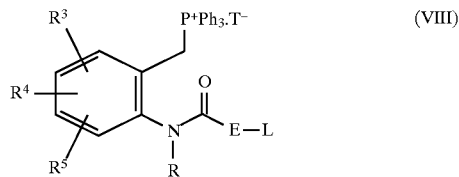

wherein R, $R^3$, $R^4$, $R^5$, E, L and T are as defined above.

The intermediates of formula VIII may in turn be conveniently prepared by reacting a compound of formula IX:

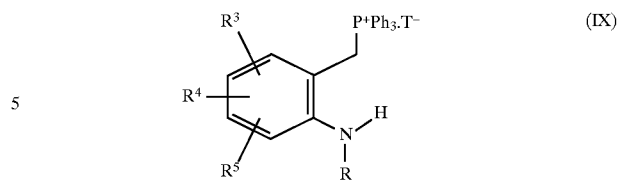

with an acylating agent of formula G—E—L; wherein R, $R^3$, $R^4$, $R^5$, E, L, G and T are as defined above.

Where they are not commercially available, the starting materials of formula III, IV, VI, IX and G—E—L may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 μM.

EXAMPLE 1

2-(2-[4-Phenylpiperazin-1-yl]ethyl)indole

Step 1: 2-(3-Chloropropionylamino) benzyltriphenylphosphonium bromide

3-Chloropropionyl chloride (3.0 ml, 32 mmol) and piperidine (3.5 ml, 43.5 mmol) were added to a suspension of 2-aminobenzyltriphenylphosphonium bromide (13.0 g, 29 mmol) (synthesised using the procedure of Capuano et al, Chem. Ber., 1986, 119, 2069–2074) in dichloromethane (60 ml) under a nitrogen atmosphere. The mixture was heated at reflux for 30 min. and then cooled to room temperature. Dichloromethane (60 ml) and hydrochloric acid (1N, 50 ml) were added and the precipitated solid was collected by filtration, washed with dichloromethane and dried in vacuo to give 2-(3-chloropropionylamino) benzyltriphenylphosphonium bromide (7.5 g, 48%). The filtrate was diluted with dichloromethane (300 ml) and washed with sodium carbonate (satd., 150 ml). Evaporation of the dichloromethane gave a residue which was triturated with ether (200 ml) and the white solid collected to afford a second crop of product (5.0 g, 32%).

Step 2: 2-(3-[4-phenylpiperazin-1-yl]propionylamino) benzyltriphenylphosphonium bromide A mixture of 2-(3-chloropropionylamino) benzyltriphenylphosphonium bromide (2.70 g, 5 mmol) and phenylpiperazine (1.70 g, 10 mmol) in acetonitrile (85 ml) was heated at reflux for 2.5 h. The mixture was cooled to room temperature and filtered and the filtrate evaporated in vacuo to give 2-(3-[4-phenylpiperazin-1-yl] propionylamino) benzyltriphenylphosphonium bromide as a white solid (3.1 g, 93%).

Step 3: 2-(2-[4-Phenylpiperazin-1-yl]ethyl)indole

The phosphonium salt (3.1 g, 4.6 mmol) was suspended in toluene (150 ml) and heated at reflux under Dean-Stark conditions for 90 min. Freshly dried potassium tert-butoxide (716 mg, 5.5 mmol) was added and the mixture was heated at reflux for 30 min. then filtered hot. The cooled filtrate was concentrated in vacuo to about 20 ml. The residue was dissolved in dichloromethane (100 ml) and extracted with hydrochloric acid (1M, 2×50 ml). The dichloromethane extract was evaporated in vacuo and the residue purified by flash chromatography using ethyl acetate as eluant. Recrystallisation from methanol gave the title compound as a white solid (18 mg, 1.3%), mp 184°–186° C.; (Found: C, 78.59; H, 7.56; N, 13.50. $C_{20}H_{23}N_3$ requires C, 78.65; H, 7.59; N, 13.76%); $\delta_H$ (DMSO-$d_6$) 2.59–2.61 (4H, m, 2×piperazinyl $CH_2$), 2.60 (2H, t, J 4.9 Hz, $CH_2CH_2N$), 2.69–2.73 (2H, m, $CH_2CH_2N$), 3.14 (4H, t, J 4.9 Hz, 2×piperazinyl $CH_2$), 6.17 (1H, s, 3-H), 6.76 (1H, t, J 7.2 Hz, ArH), 6.78–7.00 (4H, m, ArH), 7.18–7.22 (2H, m, ArH), 7.27 (1H, d, J 8.0 Hz, 4-H), 7.39 (1H, d, J 7.6 Hz, 7-H), and 10.84 (1H, br s, NH); m/z (CI$^+$, NH$_3$) 306 (M+1)$^+$.

EXAMPLE 2

2-(2-[4-Benzylpiperazin-1-yl]ethyl)indole

Step 1: Indole-2-acetic acid

A solution of lithium hydroxide (346 mg, 8.25 mmol) in water (2 ml) was added to methyl indole-2-acetate (520 mg, 2.75 mmol) (prepared using the method of Capuano et al, Chem. Ber., 1986, 119, 2069) in THF (2 ml) and methanol (6 ml) and the mixture stirred for 1 h. The mixture was concentrated in vacuo, diluted with water (20 ml) and extracted with diethyl ether (2×10 ml). The aqueous layer was carefully acidified to pH 2 with 1M HCl and extracted into dichloromethane (3×20 ml). The extracts were dried (MgSO$_4$) and evaporated in vacuo to give indole-2-acetic acid (350 mg, 72%) as a pink solid.

Step 2: 1-benzyl-4-(2-indolylacetamido)piperazine

1-Hydroxybenzotriazole (324 mg, 2.4 mmol) and triethylamine (446 μl, 3.2 mmol) were added to a solution of indole-2-acetic acid (350 mg, 2 mmol) and 1-benzylpiperazine (352 mg, 2 mmol) in THF (25 ml), followed after 5 min by 1-(3-dimethylaminopropyl)-3-ethyl carbodiimide hydrochloride (576 mg, 3 mmol) and the mixture stirred for 15 h. The mixture was concentrated in vacuo and the residue partitioned between citric acid (1M, 30 ml) and ethyl acetate (25 ml), the phases were separated and the aqueous layer extracted with ethyl acetate (2×25 ml). The combined organic layers were washed with sodium bicarbonate (satd., 2×10 ml) and brine (satd., 20 ml), dried (Na$_2$SO$_4$) and evaporated in vacuo to give 1-benzyl-4-(2-indolylacetamido)piperazine as a pink solid (200 mg, 30%), m/z (CI$^+$, NH$_3$) 334 (M+1)$^+$.

Step 3: 2-(2-[4-Benzylpiperazin-1-yl]ethyl)indole

Lithium aluminium hydride in ether (1M, 600 μl, 0.6 mmol) was carefully added to a solution of 1-benzyl-4-(2-indolylacetamido)piperazine (200 mg, 0.6 mmol) in THF (10 ml) and the mixture was stirred at reflux for 1 h. The reaction was cooled in ice and successively treated with water (0.5 ml), sodium hydroxide (4M, 0.5 ml) and water (1.5 ml). The mixture was filtered and the filtrate concentrated in vacuo. The residue was purified by column chromatography on silica (90:8:1 CH$_2$Cl$_2$/MeOH/NH$_3$), the resulting gum dissolved in methanol and ether and treated with oxalic acid to give a brown solid (32 mg, 11%). M.p. 215°–216° C. (MeOH); (Found: C, 59.60; H, 5.99; N, 7.92. $C_{21}H_{25}N_3$.2(CO$_2$H)$_2$.0.3H$_2$O requires C, 59.47; H, 5.91; N, 8.32%); $\delta_H$ (DMSO-$d_6$) 2.78 (3H, br s, piperazinyl H), 3.06 (7H, m), 3.76 (2H, s, CH$_2$), 6.22 (1H, s, 3-H), 6.93 (1H, t, J 7.3 Hz, ArH), 7.01 (1H, m, ArH), 7.28–7.43 (7H, m, ArH), and 11.01 (1H, br s, NH); m/z (CI$^+$, NH$_3$) 320 (M+1)$^+$.

EXAMPLE 3

2-(4-Benzylpiperazin-1-ylmethyl)indole

Step 1: 2-(4-benzylpiperazin-1-yl)carbonyl indole hydrochloride

Thionyl chloride (1.62 ml, 22.3 mmol) was added to a solution of indole-2-carboxylic acid (3.0 g, 18.6 mmol) in toluene (40 ml), the mixture heated at reflux for 3 h and then cooled to room temperature. 1-Benzylpiperazine (3.7 ml, 20.4 mmol) was added and the resultant precipitate collected by filtration, washed with toluene, and dried in vacuo to give 2-(4-benzylpiperazin-1-yl) carbonyl indole hydrochloride (6.5 g, 98%). M.p. >210° C. (dec).

Step 2: 2-(4-Benzylpiperazin-1-ylmethyl)indole

Lithium aluminium hydride in THF (1M, 11.25 mmol) was slowly added to a suspension of 2-(4-benzylpiperazin-1-yl)carbonyl indole hydrochloride (2.0 g, 5.6 mmol) in THF (40 ml) under a nitrogen atmosphere and the resultant solution heated at reflux for 90 min. The mixture was cooled to room temperature and treated sequentially with water (0.5 ml), sodium hydroxide (4M, 0.5 ml) and water (1.5 ml). The mixture was filtered and the filtrate evaporated in vacuo. The residue was recrystallised from toluene to afford the title compound as a white solid (428 mg, 25%), m.p. 157°–159° C.; (Found: C, 78.44; H, 7.63; N, 13.66. $C_{20}H_{23}N_3$ requires C, 78.65; H, 7.59; N, 13.76%); $\delta_H$ (DMSO-$d_6$) 2.40 (8H, br s, 4×piperazinyl $CH_2$), 3.45 (2H, s, $CH_2$), 3.59 (2H, s, $CH_2$), 6.23 (1H, s, 3-H), 6.90 (1H, m, ArH), 6.95 (1H, m, ArH), 7.20–7.32 (6H, m, ArH), 7.42 (1H, d, J 7.7 Hz, ArH), and 10.93 (1H, br s, NH); m/z ($CI^+$, $NH_3$) 306 $(M+1)^+$.

The following were prepared in an analogous manner:

EXAMPLE 4

2-(4-Phenylpiperazin-1-ylmethyl)indole

M.p. 264° C. (toluene); (Found: C, 78.68; H, 7.35; N, 14.33. $C_{19}H_{21}N_3$ requires C, 78.32; H, 7.26; N, 14.42%); $\delta_H$ (DMSO-$d_6$) 2.55 (4H, t, J 4.9 Hz, 2×piperazinyl $CH_2$), 3.14 (4H, t, J 4.9 Hz, 2×piperazinyl $CH_2$), 3.66 (2H, s, $CH_2$—N), 6.29 (1H, s, 3-H), 6.75 (1H, t, J 7.3 Hz, ArH), 6.89–6.95 (3H, m, ArH), 7.00 (1H, m, ArH), 7.16–7.24 (2H, m, ArH), 7.32 (1H, d, J 7.2 Hz), 7.44 (1H, d, J 7.2 Hz, ArH), and 11.00 (1H, br s, NH); m/z ($CI^+$, $NH_3$) 292 $(M+1)^+$.

EXAMPLE 5

2-(4-[4-Chlorophenyl]piperazin-1-ylmethyl)indole hydrogen oxalate

M.p. 220° C. (dec) (MeOH/$H_2O$); (Found: C, 60.25; H, 5.23; N, 9.67. $C_{19}H_{20}N_3Cl$. $(CO_2H)_2$ requires C, 60.65; H, 5.33; N, 10.10%); $\delta_H$ (DMSO-$d_6$) 2.77 (4H, m, 2×piperazinyl $CH_2$), 3.22 (4H, m, 2×piperazinyl $CH_2$), 3.91 (2H, s, $NCH_2$), 6.40 (1H, s, 3-H), 6.93–6.99 (3H, m, ArH), 7.06 (1H, t, J 7.3 Hz, ArH), 7.23 (2H, m, ArH), 7.35 (1H, d, J 7.6 Hz, 4-H), 7.49 (1H, d, J 7.5 Hz, 7-H), and 11.13 (1H, br s, NH); m/z ($CI^+$, $NH_3$) 326 $(M+1)^+$.

EXAMPLE 6

2-(4-Phenyl-1,2,3,6-tetrahydropyridin-1-ylmethyl) indole

M.p. 128°–130° C. (EtOAc); (Found: C, 82.14; H, 6.89; N, 9.46. $C_{20}H_{20}N_2$. 0.25$H_2O$ requires C, 82.02; H, 7.06; N, 9.56%); $\delta_H$(DMSO-$d_6$) 2.48–2.50 (2H, m, $NCH_2CH_2$), 2.69 (2H, t, J 5.6 Hz, $NCH_2CH_2$), 3.11 (2H, d, J 3.0 Hz, $NCH_2$—CH=), 3.73 (2H, s, $NCH_2Ar$), 6.15 (1H, m, $NCH_2$—CH=), 6.30 (1H, s, 3-H), 6.93 (1H, m, ArH), 6.99–7.04 (1H, m, ArH), 7.23 (1H, t, J 7.2 Hz, ArH), 7.29–7.34 (3H, m, ArH), 7.40–7.45 (3H, m, ArH), and 11.03 (1H, br s, NH); m/z ($CI^+$, $NH_3$) 289 $(M+1)^+$.

EXAMPLE 7

2-(4-[4-Methoxyphenyl]piperazin-1-ylmethyl)indole hydrogen oxalate

M.p. 218°–220° C. (dec) (MeOH); (Found: C, 64.55; H, 6.10; N, 9.95. $C_{20}H_{23}N_3O$. $(CO_2H)_2$ requires C, 64.22; H, 6.12; N, 10.21%); $\delta_H$ (DMSO-$d_6$) 2.89 (4H, br s, 2×piperazinyl $CH_2$); 3.14 (4H, br s, 2×piperazinyl $CH_2$), 3.67 (3H, s, $OCH_3$), 4.05 (2H, s, $NCH_2Ar$), 6.46 (1H, s, 3-H), 6.81 (2H, d, J 9.1 Hz, ArH), 6.90 (2H, d, J 9.1 Hz, ArH), 6.99 (1H, t, J 7 Hz, indole-H), 7.08 (1H, t, J 7 Hz, indole-H), 7.37 (1H, d, J 8 Hz, 4-H), 7.51 (1H, d, J 8 Hz, 7-H), 11.25 (1H, br s, NH); m/z ($CI^+$, $NH_3$) 322 $(M+1)^+$.

EXAMPLE 8

2-(4-[2-Phenylethyl]piperidin-1-ylmethyl)indole hydrogen oxalate

M.p. 230°–232° C. (dec) (MeOH); (Found: C, 69.98; H, 6.87; N, 6.81. $C_{22}H_{26}N_2$. $(CO_2H)_2$. 0.25$H_2O$ requires C, 69.80; H, 6.96; N, 6.78%); $\delta_H$ (DMSO-$d_6$) 1.38 (3H, m, aliphatic H), 1.51 (2H, m, aliphatic H), 1.86 (2H, m, aliphatic H), 2.55 (2H, m, aliphatic H), 2.67 (2H, m, aliphatic H), 3.22 (2H, m, aliphatic H), 4.19 (2H, s, $NCH_2Ar$), 6.52 (1H, s, 3-H), 6.98–7.02 (1H, m, ArH), 7.09–7.19 (4H, m, ArH), 7.24–7.28 (2H, m, ArH), 7.40 (1H, d, J 9 Hz, 4-H), 7.53 (1H, d, J 8 Hz, 7-H), and 11.28 (1H, br s, NH); m/z ($CI^+$, $NH_3$) 319 $(M+1)^+$.

EXAMPLE 9

2-(4-[Benzyloxy]piperidin-1-ylmethyl)indole

M.p. 103°–105° C. (MeOH); (Found: C, 78.33; H, 7.48; N, 8.56. $C_{21}H_{24}N_2O$ requires C, 78.71; H, 7.55; N, 8.74%); $\delta_H$ (DMSO-$d_6$) 1.54 (2H, m, piperidinyl $CH_2$), 1.85 (2H, m, piperidinyl $CH_2$), 2.12 (2H, t, J 9 Hz, piperidinyl $CH_2$), 2.71 (2H, m, piperidinyl $CH_2$), 3.39 (1H, m, piperidinyl CH), 3.57 (2H, s, $NCH_2Ar$), 4.48 (2H, s, $OCH_2Ph$), 6.24 (1H, s, 3-H), 6.92 (1H, m, ArH), 7.00 (1H, m, ArH), 7.23–7.35 (6H, m, ArH), 7.42 (1H, d, J 7.7 Hz, 7-H), and 10.94 (1H, br s, NH); m/z ($CI^+$, $NH_3$) 321 $(M+1)^+$.

EXAMPLE 10

2-(4-[2-Phenylethyl]-1,2,3,6-tetrahydropyridin-1-ylmethyl) indole hydrogen oxalate hemihydrate M.p. 226°–228° C. (dec) (MeOH); (Found: C, 69.59; H, 6.23; N, 6.71. $C_{22}H_{24}N_2.(CO_2H)_2.0.5H_2O$ requires C, 69.38; H, 6.55; N, 6.74%), $\delta_H$ (DMSO-$d_6$) 2.27 (4H, m, 2×$CH_2$), 2.69 (2H, m, $CH_2$), 3.04 (2H, br s, $CH_2$), 3.27 (2H, br s, $CH_2$), 4.20 (2H, s, $NCH_2Ar$), 5.41 (1H, S, $NCH_2$—CH=), 6.51 (1H, s, 3-H), 7.00 (1H, t, J 7.3 Hz, ArH), 7.08–7.37 (6H, m, ArH), 7.39 (1H, d, J 8 Hz, 4-H), 7.52 (1H, d, J 8 Hz, 7-H), and 11.34 (1H, br s, NH); m/z ($CI^+$, $NH_3$) 317 $(M+1)^+$.

EXAMPLE 11

2-(4-Phenylpropyl-1,2,3,6-tetrahydropyridin-1-ylmethyl) indole hydrogen oxalate

M.p. 208°–210° C. (EtOH); (Found: C, 71.27; H, 6.84; N, 6.56. $C_{23}H_{26}N_2$. $(CO_2H_2)$ requires C, 71.41; H, 6.71; N, 6.66%); $\delta_H$ (DMSO-$d_6$) 1.67 (2H, m, $PhCH_2CH_2CH_2$), 2.00 (2H, t, J 7.2 Hz, $CH_2$), 2.22 (2H, br s, tetrahydropyridinyl $CH_2$), 2.54 (2H, t, J 7.6 Hz, $CH_2$), 3.06 (2H, br s, tetrahydropyridinyl $CH_2$), 3.41 (2H, br s, tetrahydropyridinyl $CH_2$), 4.24 (2H, s, $NCH_2$), 5.39 (1H, s, tetrahydropyridinyl CH), 6.53 (1H, s, 3-H), 7.00 (1H, t, J 7.0 Hz, ArH), 7.09–7.19 (4H, m, ArH), 7.26 (2H, t, J 7.3 Hz, ArH), 7.39 (1H, d, J 8.0 Hz, 4-H), 7.53 (1H, d, J 7.8 Hz, 7-H), and 11.38 (1H, br s, NH); m/z ($CI^+$, $NH_3$) 331 $(M+1)^+$.

EXAMPLE 12

2-([4-(3'-Phenylpropylidene)piperidin-1-yl]methyl) indole hydrogen oxalate

M.p. 172°–174° C. (EtOH/$H_2O$); (Found: C, 71.67; H, 6.68; N, 6.74. $C_{23}H_{26}N_2$. $(CO_2H)_2$ requires C, 71.41; H, 6.71; N, 6.66%); $\delta_H$ (DMSO-d$_6$) 2.22–2.26 (6H, m, aliphatic H), 2.56–2.60 (4H, m, aliphatic H), 2.79 (2H, br s, CH$_2$), 4.08 (2H, s, NCH$_2$), 5.24 (1H, t, J 7.1 Hz, PhCH$_2$CH$_2$CH), 6.45 (1H, s, 3-H), 6.98–7.20 (7H, m, ArH), 7.39 (1H, d, J 8.1 Hz, 4-H), 7.52 (1H, d, J 7.8 Hz, 7-H), and 11.29 (1H, br s, NH); m/z (CI$^+$, NH$_3$) 331 (M+1)$^+$.

EXAMPLE 13

2-(1,2,3,4-Tetrahydroisoquinolin-2-ylmethyl)indole

M.p. 129°–131° C. (Me$_2$CO/H$_2$O); (Found: C, 81.91; H, 6.87; N, 10.57. C$_{18}$H$_{18}$N$_2$. 0.1(H$_2$O) requires C, 81.84; H, 6.94; N, 10.61%); $\delta_H$ (CDCl$_3$) 2.84 (2H, t, J 5.8 Hz, PhCH$_2$CH$_2$N), 2.94 (2H, t, J 5.8 Hz, PhCH$_2$CH$_2$N), 3.69 (2H, s, PhCH$_2$N), 3.89 (2H, s, ArCH$_2$N), 6.41 (1H, t, J 0.9 Hz, 3-H), 6.96 (1H, d, J 7.0 Hz, ArH), 7.06–7.17 (5H, m, ArH), 7.32 (1H, d, J 8.0 Hz, 4-H), 7.57 (1H, d, J 7.6 Hz, 7-H), and 8.70 (1H, br s, NH); m/z (CI$^+$, NH$_3$) 263 (M+1)$^+$.

EXAMPLE 14

2-(1,3-Dihydroisoindol-2-ylmethyl)indole

M.p. 176°–178° C. (dec) (MeOH/H$_2$O); (Found: C, 82.58; H, 6.42; N, 11.13. C$_{17}$H$_{16}$N$_2$ requires C, 82.22; H, 6.49; N, 11.28%); $\delta_H$ (CDCl$_3$) 3.97 (4H, s, 2×dihydroisoindolyl CH$_2$), 4.07 (2H, s, NCH$_2$Ar), 6.40 (1H, t, J 0.9 Hz, 3-H), 7.06–7.22 (7H, m, ArH), 7.28 (1H, dd, J 7.9, 0.8 Hz, 4-H), 7.57 (1H, m, 7-H), and 8.64 (1H, br s, NH); m/z (CI$^+$, NH$_3$)249 (M+1)$^+$.

We claim:

1. A method for the treatment of psychotic disorders comprising the step of administering to a patient in need thereof an effective amount of a compound of formula I, or a pharmaceutically acceptable salt thereof:

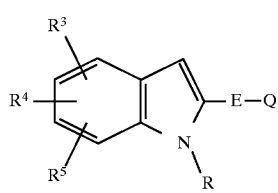

wherein

E represents —CH$_2$—;

R represents hydrogen or C$_{1-6}$ alkyl;

Q represents a moiety of formula Qa, Qb,

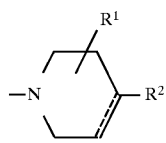

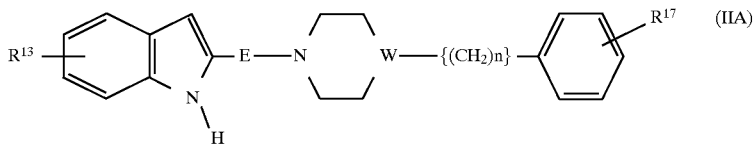

in which the broken line represents an optional chemical bond;

R$^1$ represents hydrogen;

R$^2$ represents methyl, ethyl, n-propyl, isopropyl, phenyl, chlorophenyl, ethylphenyl, methoxyphenyl, nitrophenyl, benzyl, chlorobenzyl, phenethyl, phenylpropyl or benzyloxy;

R$^3$, R$^4$ and R$^5$ independently represent hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$; wherein hydrocarbon is selected from the group consisting of: C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, aryl, aryl(C$_{1-6}$) alkyl, aryl(C$_{2-6}$)alkenyl and aryl(C$_{2-6}$)alkynyl; and heterocyclic group is selected from the group consisting of: C$_{3-7}$ heterocycloalkyl, C$_{3-7}$ heterocycloalkyl(C$_{1-6}$) alkyl, heteroaryl, heteroaryl(C$_{1-6}$)alkyl, heteroaryl (C$_{2-6}$)alkenyl and heteroaryl(C$_{2-6}$)alkynyl groups;

Z represents —CH$_2$— or —CH$_2$CH$_2$—;

R$^6$ represents hydrogen, C$_{1-6}$ alkyl, C$_{1-6}$ alkoxy, aryl, aryl(C$_{1-6}$)alkyl or halogen; and R$^a$ and R$^b$ independently represent hydrogen, hydrocarbon or a heterocyclic group, as defined above.

2. The method of claim 1 wherein said compound is represented by formula IIA, or a pharmaceutically acceptable salt thereof:

wherein

E is as defined in claim 1;

n is zero, 1, 2 or 3;

W is CH;

R$^{13}$ represents hydrogen, halogen, cyano, nitro, trifluoromethyl, amino, C$_{1-6}$ alkylamino, di(C$_{1-6}$) alkylamino, C$_{1-6}$ alkyl, C$_{1-6}$ alkoxy, aryl(C$_{1-6}$)alkoxy or C$_{2-6}$ alkylcarbonyl; and R$^{17}$ represents hydrogen, chloro, nitro or methoxy.

3. The method of claim 1 wherein said compound is represented by formula IIB, or a pharmaceutically acceptable salt thereof:

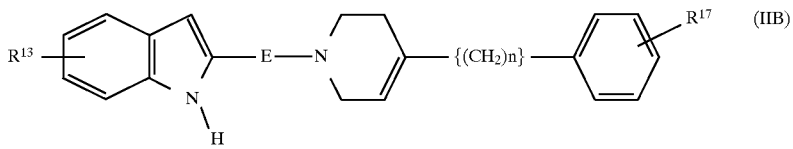

wherein
E is —CH$_2$—; and
n is zero, 1, 2 or 3;
R$^{13}$ represents hydrogen, halogen, cyano, nitro, trifluoromethyl, amino, C$_{1-6}$ alkylamino, di(C$_{1-6}$)alkylamino, C$_{1-6}$ alkyl, C$_{1-6}$ alkoxy, aryl(C$_{1-6}$)alkoxy or C$_{2-6}$ alkylcarbonyl and
R$^{17}$ represents hydrogen, chloro, nitro or methoxy.

4. The method of claim 1 wherein said compound is represented by formula IIC, or a pharmaceutically acceptable salt thereof:

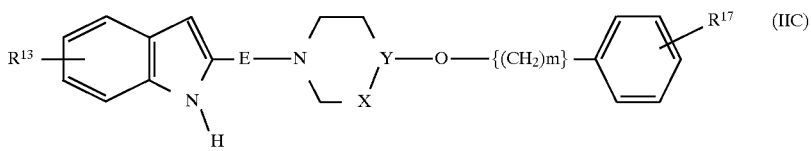

wherein
m is 1, 2 or 3;
—X—Y— represents —CH$_2$CH— or —CH=C—;
E is —CH$_2$—;
R$^{13}$ represents hydrogen, halogen, cyano, nitro, trifluoromethyl, amino, C$_{1-6}$ alkylamino, di(C$_{1-6}$)alkylamino, C$_{1-6}$ alkyl, C$_{1-6}$ alkoxy, aryl(C$_{1-6}$)alkoxy or C$_{2-6}$ alkylcarbonyl; and
R$^{17}$ represents hydrogen, chloro, nitro or methoxy.

5. The method of claim 1 wherein said compound is represented by formula IIE, or a pharmaceutically acceptable salt thereof:

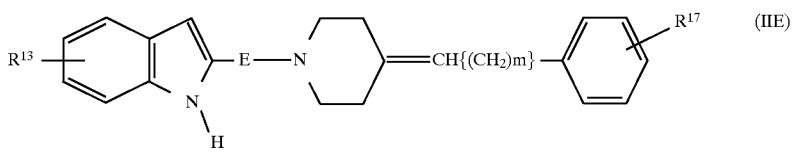

wherein
E is —CH$_2$—;
R$^{13}$ represents hydrogen, halogen, cyano, nitro, trifluoromethyl, amino, C$_{1-6}$ alkylamino, di(C$_{1-6}$)alkylamino, C$_{1-6}$ alkyl, C$_{1-6}$ alkoxy, aryl(C$_{1-6}$)alkoxy or C$_{2-6}$ alkylcarbonyl;
R$^{17}$ represents hydrogen, chloro, nitro or methoxy; and
m is 1, 2 or 3.

6. A compound of formula IIB or a pharmaceutically acceptable salt thereof:

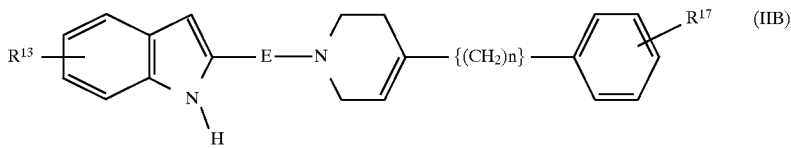

wherein

E is —CH$_2$—; and n is zero, 1, 2 or 3;

R$^{13}$ represents hydrogen, halogen, cyano, nitro, trifluoromethyl, amino, C$_{1-6}$ alkylamino, di(C$_{1-6}$)alkylamino, C$_{1-6}$ alkyl, C$_{1-6}$ alkoxy, aryl(C$_{1-6}$)alkoxy or C$_{2-6}$ alkylcarbonyl and R$^{17}$ represents hydrogen, chloro, nitro or methoxy.

7. A compound of formula IIC or a pharmaceutically acceptable salt thereof:

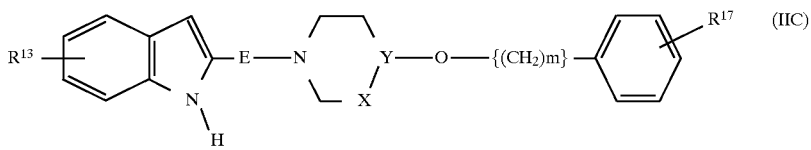

wherein m is 1, 2 or 3;

—X—Y— represents —CH$_2$CH— or —CH═C—;

E is —CH$_2$—;

R$^{13}$ represents hydrogen, halogen, cyano, nitro, trifluoromethyl, amino, C$_{1-6}$ alkylamino, di(C$_{1-6}$)alkylamino, C$_{1-6}$ alkyl, C$_{1-6}$ alkoxy, aryl(C$_{1-6}$)alkoxy or C$_{2-6}$ alkylcarbonyl and R$^{17}$ represents hydrogen, chloro, nitro or methoxy.

8. A compound of formula IIE or a pharmaceutically acceptable salt thereof:

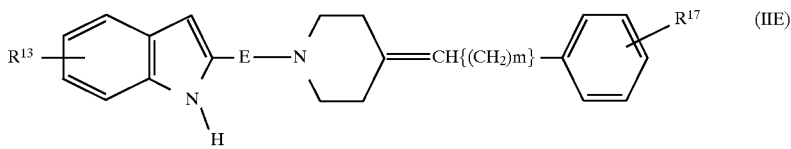

wherein

E is —CH$_2$—;

R$^{13}$ represents hydrogen, halogen, cyano, nitro, trifluoromethyl, amino, C$_{1-6}$ alkylamino, di(C$_{1-6}$)alkylamino, C$_{1-6}$ alkyl, C$_{1-6}$ alkoxy, aryl(C$_{1-6}$)alkoxy or C$_{2-6}$ alkylcarbonyl;

R$^{17}$ represents hydrogen, chloro, nitro or methoxy; and m is 1, 2 or 3.

9. A compound selected from:

2-(4-phenyl-1,2,3,6-tetrahydropyrid-1-ylmethyl)-1H-indole;

2-[4-(2-phenylethyl)piperidin-1-ylmethyl]-1H-indole;

2-(4-benzyloxypiperidin-1-ylmethyl)-1H-indole;

2-[4-(2-phenylethyl)-1,2,3,6-tetrahydropyrid-1-ylmethyl]-1H-indole;

2-[4-(3-phenylpropyl)-1,2,3,6-tetrahydropyrid-1-ylmethyl]-1H-indole;

2-[4-(3-phenylpropylidene)piperidin-1-ylmethyl]-1H-indole;

or a pharmaceutically acceptable salt thereof.

10. A pharmaceutical composition comprising an effective amount of a compound as defined in claim 6, or a pharmaceutically acceptable salt thereof, in association with a pharmaceutically acceptable carrier.

11. A pharmaceutical composition comprising an effective amount of a compound as defined in claim 7, or a pharmaceutically acceptable salt thereof, in association with a pharmaceutically acceptable carrier.

12. A pharmaceutical composition comprising an effective amount of a compound as defined in claim 9, or a pharmaceutically acceptable salt thereof, in association with a pharmaceutically acceptable carrier.

13. A pharmaceutical composition comprising an effective amount of a compound as defined in claim 10, or a pharmaceutically acceptable salt thereof, in association with a pharmaceutically acceptable carrier.

* * * * *